(12) United States Patent
Fedouloff et al.

(10) Patent No.: US 6,583,294 B2
(45) Date of Patent: Jun. 24, 2003

(54) PROCESS FOR THE PREPARATION OF AN INDOLE DERIVATIVE

(75) Inventors: Michael Fedouloff, London (GB); John Bryce Strachan, Bishop's Stortford (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/308,474

(22) Filed: Dec. 3, 2002

(65) Prior Publication Data

US 2003/0083506 A1 May 1, 2003

Related U.S. Application Data

(63) Continuation of application No. 09/743,820, filed as application No. PCT/EP99/04944 on Jul. 13, 1999.

(30) Foreign Application Priority Data

Jul. 16, 1998 (GB) .............................................. 9815481

(51) Int. Cl.⁷ ............................................ C07D 209/34
(52) U.S. Cl. ...................................................... 548/486
(58) Field of Search ......................................... 548/486

(56) References Cited

U.S. PATENT DOCUMENTS 5,852,014 A    12/1998  Gaster et al.
5,998,409 A    12/1999  Gaster et al.

FOREIGN PATENT DOCUMENTS

| EP | 0884319 A2 | | 12/1998 |
|---|---|---|---|
| GB | WO 98/07728 | | 2/1998 |
| WO | WO 93/18036 | | 9/1993 |
| WO | WO 98/07728 | * | 2/1998 |
| WO | WO 98/11067 | | 3/1998 |
| WO | WO 99/29697 | | 6/1999 |
| WO | WO 00/03983 | | 1/2000 |

OTHER PUBLICATIONS

L.M. Gaster, et al., *J. Med. Chem.*, 38(24), 1995, pp. 4760–4763.

L. Gaster, *Drugs of the Future*, 1997, 22(12), pp. 1325–1332.

K.A. Wardle, et al., Br. J. Pharmacol., 1996, 118, pp665–670.

* cited by examiner

*Primary Examiner*—Alan L. Rotman
*Assistant Examiner*—Binta Robinson
(74) *Attorney, Agent, or Firm*—Soma G. Simon; Mary E. McCarthy; Charles M. Kinzig

(57) ABSTRACT

A process for the preparation of methyl 2-(3-chloropropoxy)-indole-3-carboxylate, which comprises reacting a 3-chloro-3-carboxylate indole compound with 3-chloropropanol in the presence of an acid having a pKa of from 0 to 2.

2 Claims, No Drawings

PROCESS FOR THE PREPARATION OF AN INDOLE DERIVATIVE

This is a continuation of application Ser. No. 09/743,820 filed Jan. 16, 2001, which is a 371 of PCT/EP99/04944 filed Jul. 13, 1999, which claims priority to GB9815481.8 filed Jul. 16, 1998.

This invention relates to a new synthetic process to a compound having pharmacological activity.

WO 93/18036 (SmithKline Beecham plc) describes certain indole compounds having 5-HT$_4$ receptor antagonist activity including the compound of formula (I)

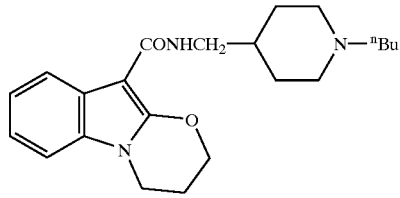

and its pharmaceutically acceptable salts. This compound is N-[(1-$^n$butyl4-piperidyl)methyl]-3,4-dihydro-2H-[1,3] oxazino[3,2-a]indole-10-carboxamide, referred to herein by its code number SB-207266, (the hydrochloride salt is SB-207266-A), which is being developed by SmithKline Beecham plc as the active ingredient in a medicament for treatment of irritable bowel syndrome.

Example 3 of WO 93/18036 describes a method of preparation of SB-207266-A from N-[(1-$^n$butyl-4-piperidyl) methyl]indole-3-carboxamide (i.e. the compound corresponding to SB-207266, without the oxazino moiety), by reacting with N-chlorosuccinimide and 3-bromo-1-propanol, followed by treatment with sodium carbonate. N-[(1-$^n$butyl-4-piperidyl)methyl]indole-3-carboxamide is prepared by coupling N-(1-$^n$butyl-4-piperidyl)methylamine with a indole-3-carboxylic acid.

WO 98/07728 (SmithKline Beecham plc) describes a process for preparing SB-207266-A which involves the use of the N-(1-$^n$butyl-4-piperidyl)methylamine intermediate at a later stage in the process thus resulting in an increased yield of SB-207266-A relative to the amount of this intermediate, which is relatively expensive to produce. In particular, the alternative process comprises the reaction of of N-(1-$^n$butyl-4-piperidyl)methylamine with a compound of formula (A):

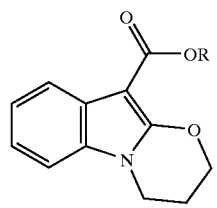

wherein R is alkyl, such as methyl or ethyl.

The compound of formula (A) wherein R is methyl is methyl 3,4-dihydro-2H-[1,3]-oxazino[3,2-a]indole-10-carboxylate.

WO98/07728 also describes the preparation of the oxazinoindole compound of the formula (A) from the corresponding indole by reaction with N-chlorosuccinimide and a 3-halo-propanol, such as 3-chloropropanol or 3-bromopropanol followed by cyclisation of the intermediate (B) by treatment with base in a suitable solvent.

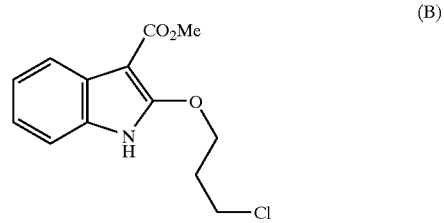

The Description in the latter specification describes in more detail the the preparation of compound (B) from the corresponding methyl indole-3-carboxylate by reaction of the latter with N-chlorosuccinimide in the presence of 1,4-diazabicyclo[2.2.2]octane (DABCO) to form an intermediate of formula (C):

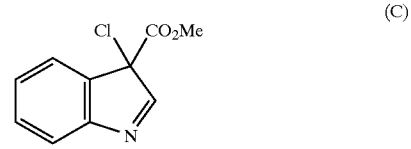

and subsequent reaction of (C) with 3-chloropropanol in the presence of methanesulphonic acid.

We have now found that the use of an acid having a pKa of from 0 to 2, especially trichloroacetic acid, in place of methanesulphonic acid results in significant advantages for the commercial operation of the process.

According to a feature of the present invention we provide a process for the preparation of the compound of formula (B) above, namely methyl 2-(3-chloropropoxy)-indole-3-carboxylate, which comprises reacting a compound of formula (C) with 3-chloropropanol in the presence of an acid having a pKa of from 0 to 2, especially trichloroacetic acid.

Other acids which may be used in accordance with the invention in addition to trichloroacetic acid include dichloroacetic acid and trifluoroacetic acid.

The use of the above-defined acid such as trichloroacetic acid in place of methanesulphonic acid has been found to increase significantly the overall yield of the process. The former acid also has the advantage over the latter that its use results in the formation of lower levels of the corresponding 2-methoxy compound, as an impurity.

The reaction is conveniently effected in an organic solvent such as dichloromethane or chloroform, at a temperature in the range –20° C. to +10° C., for example using a catalytic amount of the acid. The resulting product of formula (B) can be used for the next stage in the synthesis of SB-207266 e.g as described in WO 98/07728.

The following Example illustrates the invention.

EXAMPLE

Methyl 2-(3-chloropropoxy)-indole-3-carboxylate (formula (B)) A mixture of methyl indole-3-carboxylate and dichloromethane is cooled to 0° C. 1,4-dimethylpiperazine (0.55eq.) and N-chlorosuccinimide (1.1 eq) are added and the mixture left to stir for two hours to give a slurry containing the compound of formula (C) above. The resulting slurry is added to a solution of 3-chloropropanol (1.1 eq) and trichloroacetic acid (0.12 eq) in dichloromethane, maintaining the temperature below 0° C. The reaction mixture is left to stir for half an hour, then washed with 10% aqueous sodium carbonate, 0.5 M hydrochloric acid and water. The organic solution is dried over sodium sulphate, filtered and the solvent evaporated. Toluene is added and the mixture stirred at 0–5° C. for one hour. The product is then filtered, washed with toluene and dried to give the title product in 83% yield.

What is claimed is:

1. A process for the preparation of methyl 2-(3-chloropropoxy)-indole-3-carboxylate, which comprises reacting a compound of formula (C)

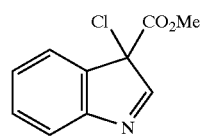

(C)

with 3-chloropropanol in the presence of an acid having a pKa of from 0 to 2.

2. A process as claimed in claim 1 in which the acid is trichloroacetic acid.

* * * * *